(12) United States Patent
Jiang et al.

(10) Patent No.: US 8,463,356 B2
(45) Date of Patent: Jun. 11, 2013

(54) ULTRASONIC THERAPY SYSTEM REDUCING THE ELECTROMAGNETIC INTERFERENCE TO THE IMAGING DEVICE

(75) Inventors: Guanghong Jiang, Chongqing (CN); Huachang Qin, Chongqing (CN); Yingshu Fu, Chongqing (CN); Youxiang Peng, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 901 days.

(21) Appl. No.: 12/445,355

(22) PCT Filed: Feb. 14, 2007

(86) PCT No.: PCT/CN2007/000545
§ 371 (c)(1),
(2), (4) Date: Apr. 13, 2009

(87) PCT Pub. No.: WO2008/046276
PCT Pub. Date: Apr. 24, 2008

(65) Prior Publication Data
US 2010/0076351 A1 Mar. 25, 2010

(30) Foreign Application Priority Data
Oct. 16, 2006 (CN) .......................... 2006 1 0150289

(51) Int. Cl.
*A61B 5/05* (2006.01)
(52) U.S. Cl.
USPC ............ 600/411; 600/407; 600/410; 600/437

(58) Field of Classification Search
USPC .................. 600/407, 437, 410, 411; 601/1, 2, 601/3
See application file for complete search history.

(56) References Cited

U.S. PATENT DOCUMENTS

| | | | |
|---|---|---|---|
| 4,712,560 A * | 12/1987 | Schaefer et al. | 600/413 |
| 5,443,068 A * | 8/1995 | Cline et al. | 600/411 |
| 5,494,036 A | 2/1996 | Uber, III et al. | |
| 5,573,000 A * | 11/1996 | Goffer et al. | 600/410 |
| 5,991,700 A * | 11/1999 | Clay et al. | 702/131 |
| 6,218,836 B1 * | 4/2001 | Vrijheid | 324/318 |
| 6,418,337 B1 * | 7/2002 | Torchia et al. | 600/411 |
| 2002/0021428 A1 * | 2/2002 | Nakano et al. | 355/53 |
| 2006/0104422 A1 | 5/2006 | Iisaku et al. | |
| 2008/0275330 A1 | 11/2008 | Mu et al. | |

FOREIGN PATENT DOCUMENTS

| CN | 1781455 A | 6/2006 |
|---|---|---|
| CN | 1814320 A | 8/2006 |

* cited by examiner

*Primary Examiner* — Tse Chen
*Assistant Examiner* — Jason Ip
(74) *Attorney, Agent, or Firm* — The Webb Law Firm

(57) ABSTRACT

An ultrasonic therapy system capable of reducing the electromagnetic interference to the imaging device includes an imaging device, an ultrasonic therapy device and an electric controlling unit. The ultrasonic therapy device includes an ultrasonic therapy applicator and the movement positioning units thereof. Driving motors for controlling the movement of the ultrasonic therapy applicator are provided in the movement positioning units, wherein the driving motors are disposed outside the area where the electromagnetic wave of the driving motors can interfere with the imaging device, and the driving motors are connected to the ultrasonic therapy applicator through gearing units.

11 Claims, 3 Drawing Sheets

ULTRASONIC THERAPY SYSTEM REDUCING THE ELECTROMAGNETIC INTERFERENCE TO THE IMAGING DEVICE

FIELD OF THE INVENTION

The present invention pertains to the field of ultrasonic therapy, relates to an ultrasonic therapy system guided by an imaging device and specifically, to an ultrasonic therapy system capable of reducing electromagnetic interference to the imaging device.

BACKGROUND OF THE INVENTION

The existing ultrasonic therapy system combines an imaging device with an ultrasonic therapy device, thereby a whole diagnosis and treatment plan with higher quality and higher efficiency can be provided to the patients.

Because an MRI apparatus can provide safe, fast and accurate imaging, as an imaging device to guide an ultrasonic therapy device, the MRI apparatus has been applied more widely in clinical diagnosis. However, the driving motors in the ultrasonic therapy device and the high-frequency generators in the ultrasonic therapy applicator as main electromagnetic interference sources may cause great electromagnetic interference to the imaging of MRI apparatus.

In ultrasonic therapy device, the movement positioning unit of the ultrasonic therapy applicator includes multiple driving motors to drive the focal point of the ultrasonic therapy applicator to move in three-dimensions.

As shown in FIG. 1, the motor for treatment bed 4 drives the treatment bed (not illustrated in FIG. 1) and the focal point moving board 14. It drives the treatment bed to go into or withdraw from the bore of the MRI apparatus. Focal point moving board 14 carries X, Y and Z-boards and the X, Y and Z-driving motors to approach or keep away from MRI apparatus.

The Z-driving motor 3 for Z-board is fixed on focal point moving board 14. Z-board 13 is mounted on focal point moving board 14 and it can move in Z-direction relatively.

The Y-driving motor 2 for Y-board is fixed on Z-board 13. Y-board 12 is mounted on Z-board 13 and it can move in Y-direction relatively to Z-board 13.

The X-driving motor 1 for X-board is fixed on Y-board 12. X-board 11 is mounted on Y-board 12 and it can move in X-direction relatively to Y-board 12.

The ultrasonic therapy applicator 5 is connected to X-board 11 and moves with X-board.

The Z-driving motor 3 drives Z-board 13 to move in Z-direction through Z-gearing unit (not illustrated in FIG. 1). Z-board drives Y-board 12, Y-driving motor 2, X-board 11, X-driving motor 1 and ultrasonic therapy applicator 5 to move in Z-direction. The Y-driving motor drives Y-board to move in Y-direction through Y-gearing unit (not illustrated in FIG. 1). Y-board drives X-driving motor 1, X-board 11 and ultrasonic therapy applicator 5 to move in Y-direction. The X-driving motor 1 drives X-board 11 to move in X-direction through X-gearing unit (not illustrated in FIG. 1). X-board drives ultrasonic therapy applicator 5 to move in X-direction.

This shows that the driving motors for X, Y and Z-boards will move correspondingly during the movement of the focal point of the ultrasonic therapy applicator 5. Because these motors are close to MRI imaging zone, the electromagnetic interference occurred when these driving motors work and the ferromagnetic substances contained in the motors when these motors are moving will cause great interference to the MRI imaging.

During diagnosis and treatment, the electric control unit and the high-frequency generator for supplying power to ultrasonic therapy applicator 5 of the ultrasonic therapy system will bring great interference to MRI imaging.

During MRI imaging, the factors of electromagnetic interference as above mentioned will seriously influence the accuracy of MRI imaging. Therefore, the effects of diagnosis and treatment will be influenced.

So, for an imaging device, especially for an MRI-guided ultrasonic therapy system, to reduce the electromagnetic interference is critical to the whole therapy system.

SUMMARY OF THE INVENTION

Aiming at the disadvantages of the prior art as mentioned above, the technical problem to be solved in the present invention is to provide an ultrasonic therapy system, which can effectively reduce electromagnetic interference to an imaging device. Accordingly, an ultrasonic system with an electromagnetic compatibility between an ultrasonic therapy device and an imaging device (MRI apparatus) can be realized.

The technical solution for the problems proposed by the present invention is as follows: the ultrasonic therapy system capable of reducing electromagnetic interference to the imaging device comprises an imaging device, ultrasonic therapy device and electric control unit. The ultrasonic therapy device comprises an ultrasonic therapy applicator and its movement positioning unit. Said movement positioning unit, comprises driving motors to control the movement of the ultrasonic therapy applicator. Wherein, the driving motor is disposed beyond the area, in which the electromagnetic waves of the motors can bring electromagnetic interference to the imaging device. The driving motor is connected to the ultrasonic therapy applicator through a gearing unit.

The impetus of rotation of driving motor may be transmitted to a gearing unit through a long shaft and then it is transmitted to the ultrasonic therapy applicator from the gearing unit. Thus, the driving motor can be arranged far away from the imaging area of the MRI apparatus so that the electromagnetic interference to the imaging device can be avoided.

The driving motors are disposed beyond the place, which is 2 meters away from the central point of imaging area of the imaging device.

Said movement positioning unit may comprise X-board and the ultrasonic therapy applicator is placed on the X-board. The driving motor is connected to X-board through X-gearing unit and said driving motor is the X-driving motor to drive X-board to move in X-direction.

Said movement positioning unit may further comprise Y-board and the Y-driving motor, which is used to drive Y-board to move in Y-direction. Said X-board is placed on the Y-board. The Y-driving motor is placed 2 meters away from the central point of imaging area of the imaging device and it is connected to Y-board through Y-gearing unit.

Said movement positioning unit may further comprise Z-board and the Z-driving motor, which is used to drive Z-board to move in Z-direction. Said Y-board is placed on the Z-board. The Z-driving motor is placed 2 meters away from the central point of imaging area of the imaging device and it is connected to Z-board through Z-gearing unit.

In order to make ultrasonic therapy applicator enter into the bore of the imaging device easily, Z-board can be placed on focal point moving board and a motor for treatment bed is used to control the movement of the focal point moving board.

All driving motors as mentioned above adopt the servo motors.

In the present invention, each driving motor is placed far away from the imaging area of the imaging device and the impetus is transmitted to the ultrasonic therapy applicator by each gearing unit. During the position adjusting of focal point of ultrasonic therapy applicator, the positions of all driving motors stay still. Since the driving motors are far away from the imaging area of the imaging device, the electromagnetic interference to the imaging device can be minimized to the utmost.

In the present invention, the imaging device mainly adopts MRI apparatus; certainly, other imaging devices can also be used in the present invention.

In ultrasonic therapy system, the electric control unit under working status produces electromagnetic interference, which will influence the diagnosis accuracy of imaging device. To improve the diagnosis accuracy of MRI, it is very important to reduce the electromagnetic interference produced by electric control unit in the working MRI apparatus. Therefore, the preferred electric control unit may further comprise an electric control unit for controlling the movement of treatment bed. The electric control unit for controlling the movement of treatment bed provides a position sensor, which will actuate de-energizing the electric control unit for controlling the movement of treatment bed after the treatment bed enters into the imaging area of the imaging device. After the treatment bed of ultrasonic therapy device approaches MRI apparatus, the treatment bed needs to further move into the bore of MRI apparatus for diagnosis and ultrasonic treatment. If the electric control unit for controlling the treatment bed to move into and withdraw from the bore of MRI apparatus is de-energized during the diagnosis and treatment, the electromagnetic interference to MRI apparatus produced by electric control unit under electrifying status can be reduced effectively. When the treatment bed withdraws from the bore of MRI apparatus, the electric control unit can be re-energized.

More preferably, the electric control unit further comprises multiple low-pass filters with a high attenuation rate. The filters can filter the electromagnetic waves of the power source of high-frequency generator, electric components, controller for movement system, servo driver and the power source of driving motor respectively so that the electromagnetic interference with the frequency around the working frequency of MRI apparatus can be reduced.

The filters in the present invention mainly filter the electromagnetic waves of more than 10 MHz produced by ultrasonic therapy device. The attenuation rate of the filter ranges from 80 dB to 120 dB.

For main interference sources (for example, the power source of high-frequency generator, driving motors), shielding measures have been taken. The present invention also applies cutoff wave-guide technique to the place (for example, holes of output shaft of driving motor, the place where the control signal lines entering and exiting the shielding cover) which can not be shielded due to all kinds of reasons. The cutoff wave-guide pipe can adopt simple tubular metal structure and present electric characteristics of high-pass filters. The cutoff wave-guide pipe allows the signals with frequency higher than cutoff frequency to pass and the signals with frequency lower than cutoff frequency will be blocked or attenuated. By use of this feature, the cutoff frequency of wave-guide pipe is so designed that the frequency of interference signals falls into the cutoff area of the wave-guide pipe, thus the interference signals can not go through the wave-guide pipe, in other words, the wave-guide pipe acts as electromagnetic shielding. The cutoff wave-guide pipe of the present invention can filter the interference electromagnetic waves with frequency lower than 100 MHz and its attenuation rate ranges from 80 dB to 120 dB.

The outer shell of each driving motor may be covered by a motor shielding cover, which can shield the electromagnetic waves. The cutoff wave-guide, which can bring attenuation of electromagnetic waves, is arranged on the output shaft of each driving motor, and it is connected to the motor shielding cover and earthed. The anode and cathode of each driving motor are respectively connected to filters.

Besides, the driving motors and ultrasonic therapy applicator can be placed in the shielding room for shielding the electromagnetic waves where the imaging device is also located in. Firstly, the anode and cathode of each driving motor are respectively connected to the filter located in the shielding room. Then, said filter is connected to another filter located outside of shielding room. The ultrasonic therapy applicator is connected to the high-frequency generator through a filter located outside of shielding room. The motor shielding covers and the outer shell of driving motors are respectively connected to the shielding room by way of single-point earthing. The shielding room is earthed so that the electromagnetic interference can be reduced further.

Figure 1:
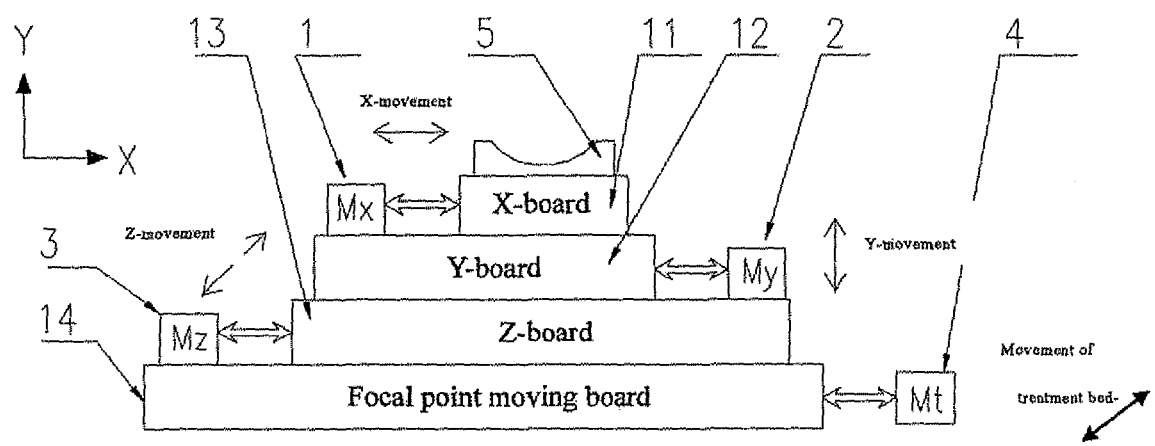
FIG. 1 is a structural diagram of movement mechanism in the ultrasonic therapy system of prior art.

Wherein: 1—X-driving motor 2—Y-driving motor 3—Z-driving motor 4—Motor for treatment bed 5—Ultrasonic therapy applicator 6—MRI apparatus 7—Treatment bed 8—Treatment bed moving unit 9—Electric control unit for movement of treatment bed 10—Movement positioning unit 11—X-board 12—Y-board 13—Z-board 14—Focal point moving board 15—Treatment bed stand 16—Electric control unit for movement positioning 17—High-frequency generator 18, 19—Driving key 20—Joining gearing part 21—X-shaft 22—Y-shaft 23—Z-shaft 24—Shielding cover for motor 25—Shielding room 26—DC power 27—Console 28—Cutoff guide-wave pipe 29—Filter 30—Matching circuit 31, 32—Cutoff guide-wave pipes 33—Motion controller 34, 35, 36, 37, 38—Filters

DETAILED DESCRIPTION OF PREFERRED EMBODIMENTS

The present invention will be further explained below in detail with reference to the preferred embodiments and accompanying drawings.

The ultrasonic therapy system of the present invention comprises an MRI apparatus 6 (imaging device), ultrasonic therapy device and electric control unit. Wherein, the ultrasonic therapy device comprises a treatment bed 7, an ultrasonic therapy applicator 5 and its movement positioning unit.

Figure 2:
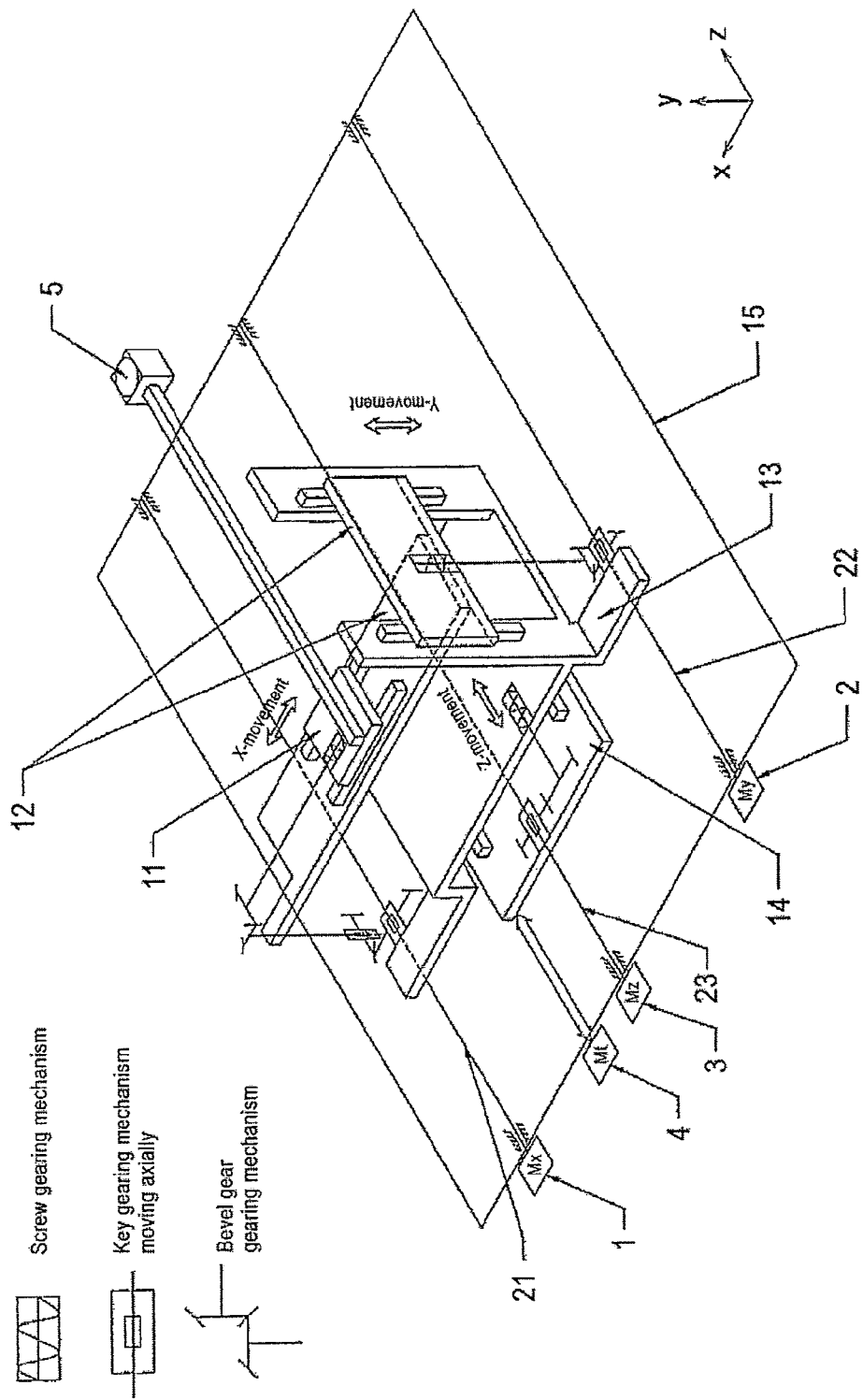
FIG. 2 is a layout of motors used in the ultrasonic therapy system of the present invention.

As shown in FIG. 2, the movement positioning unit of the ultrasonic therapy applicator 5 includes X-board 11, on which the ultrasonic therapy applicator 5 is placed, X-driving motor 1 connected to X-board 11 through X-gearing unit, Y-board 12, Y-driving motor 2 connected to Y-board 12 through Y-gearing unit, Z-board 13, Z-driving motor 3 connected to Z-board 13 through Z-gearing unit, focal point moving board 14 and the motor for treatment bed 4 for driving the focal point moving board 14 in Z-direction.

X-board 11 is mounted on Y-board 12 and Y-board 12 is connected to Z-board 13 and Z-board 13 is placed on focal point moving board 14.

In this embodiment, X-driving motor 1, Y-driving motor 2 and Z-driving motor 3 are placed on treatment bed stand 15 and they are normally 2 meters away from the central point of imaging area of MRI. X-driving motor 1, Y-driving motor 2 and Z-driving motor 3 are respectively connected to X, Y and Z-gearing units through X-shaft 21, Y-shaft 22 and Z-shaft 23. In this embodiment, all the driving motors can adopt servo motors. X-shaft 21, Y-shaft 22 and Z-shaft 23 all adopt long shafts. When the long shaft rotates, it transfers impetus to the gearing unit and when the long shaft is at rest, the gearing unit may move axially relative to the long shaft. Both sides of X-shaft 21, Y-shaft 22 and Z-shaft 23 are mounted on treatment bed stand 15. The ultrasonic therapy applicator 5 is connected to X-board 11 and moves with X-board 11.

The X-gearing unit comprises key gearing mechanism which moves along Z-direction, bevel gear gearing mechanism and screw gearing mechanism. Three gearing mechanisms transfer the impetus from X-driving motor successively. Said key gearing mechanism is connected to X-shaft 21. There is a key way opened on X-shaft 21. The length of key way is determined by the travel range of treatment bed and the travel range of focal point of ultrasonic therapy applicator in Z-direction. When Z-board 13 moves in Z-direction (i.e. the direction of bore of MRI apparatus), the key can move in the key way in Z-direction. When X-shaft 21 rotates, the impetus can be transferred to bevel gear gearing mechanism through key gearing mechanism and then transferred from bevel gear gearing mechanism to screw gearing mechanism. Finally the screw gearing mechanism drives X-board 11 to move ultrasonic therapy applicator 5 in X-direction. The screw gearing mechanism includes X-board 11 connected with bevel gear gearing mechanism by screw, a guide rail connected to Y-board 12 along X-direction. X-board 11 can move linearly in X-direction along the guide rail.

The structures of Y-gearing unit and Z-gearing unit are similar to that of X-gearing unit and the difference is the different movement directions of them.

The motor for treatment bed 4 is placed on end of treatment bed stand 15 which is far away from MRI apparatus.

The working process of said ultrasonic therapy device is as follows:

The motor for treatment bed 4 drives focal point moving board 14. The focal point moving board 14 carries Z-gearing unit mounted on it to move axially along Z-shaft 23. Z-board 13 moves with focal point moving board 14 moves and also carries Y-gearing unit and X-gearing unit to move respectively along Y-shaft 22 and X-shaft 21. Meanwhile, X-board 11, Y-board 12 and ultrasonic therapy applicator 5 followed with the treatment bed 7 enter into or withdraw from MRI.

The Z-driving motor 3 drives Z-shaft 23 to rotate. The Z-shaft 23 carries Z-board 13 to move in Z-direction through Z-gearing unit (including key gearing mechanism, bevel gear gearing mechanism and screw gearing mechanism). The Z-board 13 carries Y-board 12, Y-gearing unit, X-board 11 and X-gearing unit to move in Z-direction and accordingly drives ultrasonic therapy applicator 5 to move in Z-direction.

The Y-driving motor 2 drives Y-shaft 22 to rotate. The Y-shaft 22 carries Y-board 12 to move in Y-direction through Y-gearing unit (including key gearing mechanism, bevel gear gearing mechanism and screw gearing mechanism). The Y-board carries X-board 11, X-gearing unit to move in Y-direction and accordingly drives ultrasonic therapy applicator 5 to move in Y-direction.

The X-driving motor 1 drives X-shaft 21 to rotate. The X-shaft 21 carries X-board 11 to move in X-direction through X-gearing unit (including key gearing mechanism, bevel gear gearing mechanism and screw gearing mechanism) and accordingly drives ultrasonic therapy applicator 5 to move in X-direction.

The X, Y, Z-driving motors drive the focal point of ultrasonic therapy applicator 5 to move respectively in X, Y, Z-dimensional space. During the ultrasonic therapy, the positions of three motors keep unchanged.

The driving motors are located far away from the imaging area of MRI apparatus so that the electromagnetic interference to MRI when the driving motors are working can be reduced, and the electromagnetic interference to MRI apparatus during treatment can be avoided when driving motors are moving.

Figure 3:
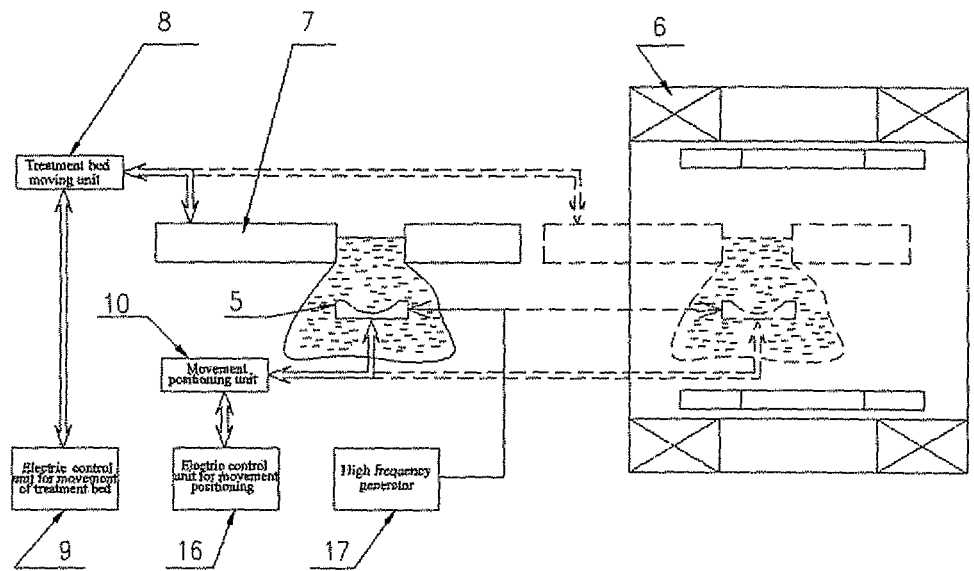
FIG. 3 is a structural diagram of electric control unit of the present invention.

As shown in FIG. 3, relative to MRI apparatus 6, the ultrasonic therapy device guided by MRI can be located outside of MRI apparatus or inside the bore of MRI apparatus.

Wherein, the electric control unit comprises electric control unit for movement of treatment bed 9 and electric control unit for movement positioning 16 of ultrasonic therapy applicator. Wherein, the electric control unit for movement of treatment bed 9 is used to control treatment bed moving unit 8. The electric control unit for movement positioning 16 is used to control movement positioning unit 10 of ultrasonic therapy applicator.

A position sensor (not illustrated in figures) is installed in an appropriate place in MRI apparatus 6. This position sensor will actuate de-energizing the electric control unit for movement of treatment bed 9 after the treatment bed 7 enters into the imaging area of MRI apparatus 6.

Figure 4:
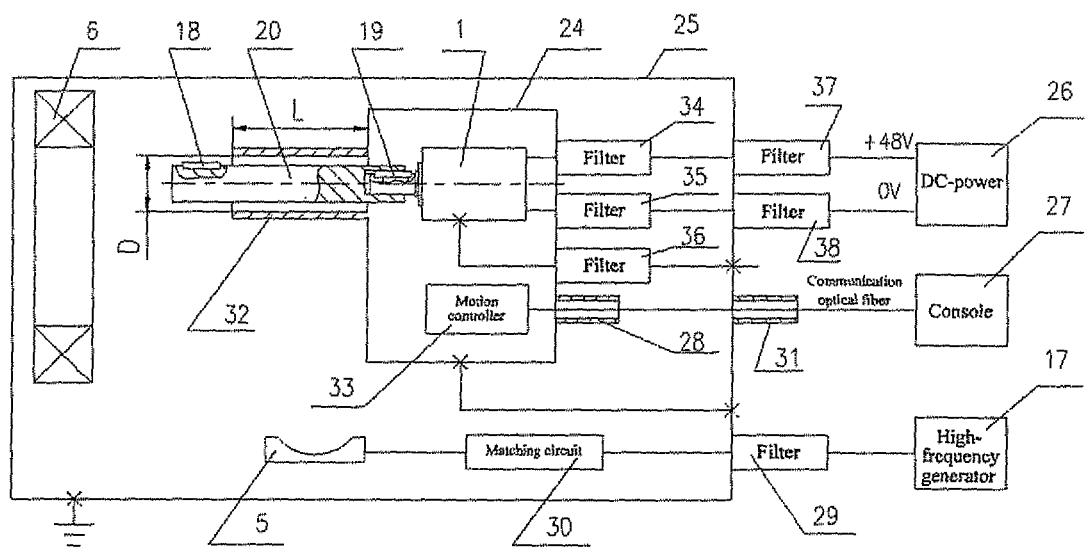
FIG. 4 is a principle diagram of shielding and filtering measures taken in the present invention.

In the present invention, for main interference sources of ultrasonic therapy system, some measures like shielding and filtering have been taken. As shown in FIG. 4, the MRI apparatus is placed in shielding room 25, which is used to shield the electromagnetic waves. The driving motors and motion controllers are also placed in shielding room 25. The DC power 26, console 27 and high-frequency generator 17 are placed outside of shielding room 25. The shielding room 25 and shielding cover for motor are made of high-permeability magnetic material with high-conductivity, which has a high performance to shield the electromagnetic waves. In this embodiment, the shielding cover for motor 24 is made of stainless steel. In the figure, the X-driving motor 1 is taken as an example.

Because the filters are used at both ends of a cable and the performance of shielding electromagnetic waves can be improved, the anode and cathode of DC power 26 are respectively connected to filter 37, filter 34 and filter 38, filter 35 for filtering and then respectively connected to the anode and cathode of X-driving motor 1. The outer shell of X-driving motor 1 is connected to shielding room 25 through filter 36 and the shielding cover for motor 24 is connected to shielding room 25. Because just in this place, the frequency of interference source to be cleared is lower than 10 MHz, the shielding cover for motor 24 and the outer shell of X-driving motor 1 are respectively connected to shielding room 25 by way of single-point earthing. The shielding room 25 is earthed.

A cutoff wave-guide pipe 32 is arranged outside of the output shaft of X-driving motor 1 (by use of electric characteristics of high-pass filters of cutoff wave-guide pipe). The cutoff wave-guide pipe 32 is connected to shielding cover for motor 24. The output shaft of X-driving motor 1 transfers the impetus by driving key 19 to joining gearing part 20. Then, the joining gearing part 20 transfers the impetus by driving key 18 to X-shaft 21 (not illustrated in the figure). The joining gearing part 20 is made of nonmetallic material. The motion controller 33 is used to control each movement positioning units and electric control unit of the present ultrasonic therapy system. The console 27 monitors motion control 33 by communication optical fiber. The cutoff wave-guide pipe 31 and cutoff wave-guide pipe 28 are respectively arranged at the places where the communication optical fiber enters into the shielding room 25 and the shielding cover for motor 24. The output power signals from high-frequency generator 17 will go through filter 29, matching circuit 30 and then to ultrasonic therapy applicator 5. Wherein, the outer shell of X-driving motor 1 (via filter 36), cutoff wave-guide pipes 28, 31 and 32, shielding cover for motor 24, shielding room 25 are single-point earthed.

In this embodiment, the filters adopt low-pass filters with a high attenuation rate. The filters mainly filter and shield the electromagnetic waves with frequency higher than 10 MHz produced by the power source and high-frequency generator. Its attenuation rate ranges from 80 dB to 120 dB. In this embodiment, filter 34, filter 35, filter 36, filter 37, and filter 38 adopt rod low-pass filters.

In this embodiment, the rod low-pass filters can filter the electromagnetic waves with frequency higher than 10 MHz with an attenuation of 100 dB. Thus, after filtering, the interference of the residual electromagnetic waves to MRI apparatus is controlled within the range, which will not influence the preciseness of MRI diagnosis. Therefore, the interference of the residual electromagnetic waves after filtering to MRI can be reduced effectively.

In this embodiment, according to the working frequency of electromagnetic waves of MRI apparatus, the frequency "f" of interference signals ranging from 10 MHz to 100 MHz is set up. According to the cutoff frequency $f_c(3\sim5)\times f$, the cutoff frequency of cutoff wave-guide pipes 31 and 32 ranging from 300 MHz to 500 MHz is set up.

For a cutoff wave-guide pipe with a round section:

$$f_c = \frac{175 \times 10^3}{D} \quad (1)$$

In formula (1):

D—Diameter of cutoff wave-guide pipe (Unit: mm)

fc—Cutoff frequency (Unit: MHz)

Attenuation "S" for a cutoff wave-guide pipe with a round section:

$$S = 32 \times \frac{L}{D} \quad (2)$$

In formula (2):

S—Attenuation value (Unit: dB)

L—Length of cutoff wave-guide pipe (Unit: mm)

D—Diameter of cutoff wave-guide pipe (Unit: mm)

In this embodiment, f is 100 MHz, fc is 500 MHz, S is 100 dB.

Under the premise to meet the relations of $$D \leq \frac{175 \times 10^3}{f_c}$$

and $$L \geq \frac{S \times D}{32}$$

and with a consideration of spatial structure, the diameter (D) and length (L) of cutoff wave-guide pipe 32 are determined as D=30 mm and L=100 mm.

By arranging cutoff wave-guide pipes on the output shaft of a driving motor, the attenuation ranging from 80 dB to 120 dB for the electromagnetic waves with frequency lower than 100 MHz can be realized and the interference to MRI can be reduced effectively.

In the process of ultrasonic diagnosis and treatment, under the control of electric control unit for movement of treatment bed 9, the treatment bed moving unit 8 drives treatment bed 7 and ultrasonic therapy applicator 5 to move into the bore of MRI apparatus 6. After the treatment bed 7 contacts with the position sensor, the electric control unit for movement of treatment bed 9 will be de-energized and the treatment bed 7 will keep stable and unchanged during ultrasonic diagnosis and treatment. The electric control unit for movement positioning 16 controls movement positioning unit 10 to drive the focal point of ultrasonic therapy applicator 5 to move in three dimensional space for applying ultrasonic therapy to the diseased part of a patient.

In the present invention, after treatment bed 7 and ultrasonic therapy applicator 5 enter into the bore of MRI apparatus 6 and before MRI apparatus 6 starts imaging, the electric control unit for movement of treatment bed 9 is de-energized and therefore, the electromagnetic interference to MRI produced by this kind of electric units under electrifying status can be avoided.

After completion of diagnosis and treatment or when the treatment bed 7 needs to be moved, the power supply to electric control unit for movement of treatment bed 9 can be resumed through switches and the treatment bed moving unit 8 is actuated to drive treatment bed 7 to move away from the bore of MRI apparatus 6.

Through cutting off the power supply to electric control unit, the electromagnetic interference to MRI apparatus 6 can be reduced effectively.

Thus, the ultrasonic therapy system of the present invention can reduce a lot of electromagnetic interference and the electromagnetic compatibility of ultrasonic therapy device and MRI apparatus can be truly realized.

The invention claimed is:

1. An ultrasonic therapy system adapted to reduce electromagnetic interference to an imaging device, said system comprising an imaging device, an ultrasonic therapy device and an electric control unit; wherein the ultrasonic therapy device comprises an ultrasonic therapy applicator and its movement positioning unit, and in said movement positioning unit, there is one or more driving motors to control the movement of the ultrasonic therapy applicator; wherein each driving motor is disposed beyond an area in which the electromagnetic waves of the driving motors can bring electromagnetic interference to the imaging device; wherein each driving motor is connected to the ultrasonic therapy applicator through a gearing unit; an outer shell of each driving motor is covered by a motor shielding cover, which shields the electromagnetic waves, and wherein a cutoff wave-guide pipe, which brings attenuation of electromagnetic waves, is arranged on an output shaft of each driving motor and is connected to the motor shielding cover at one end and is grounded; said movement positioning unit further comprises an X-board and the ultrasonic therapy applicator is placed on the X-board; a driving motor is connected to the X-board through an X-gearing unit, and the driving motor is the X-driving motor to drive the X-board to move in X-direction; said movement positioning unit further comprises a Y-board and a Y-driving motor which is used to drive the Y-board to move in a Y-direction; with said X-board placed on the Y-board, and a Y-driving motor is connected to the Y-board through a Y-gearing unit; and said movement positioning unit further comprises a Z-board and a Z-driving motor which is used to drive the Z-board to move in a Z-direction; with said Y-board placed on the Z-board, and a Z-driving motor is connected to the Z-board through a Z-gearing unit.

2. The ultrasonic therapy system of claim 1, wherein each driving motor is beyond a location which is two meters away from a central point of an imaging area of the imaging device.

3. The ultrasonic therapy system of claim 1, wherein the Z-board is placed on a focal point moving board and a motor for a treatment bed is used to control the movement of the focal point moving board.

4. The ultrasonic therapy system of claim 1, wherein the driving motors and ultrasonic therapy applicator are placed in a shielding room of the imaging device, which shields the electromagnetic waves; and wherein the motor shielding covers and the outer shells of the driving motors are respectively connected to the shielding room by way of single-point grounding and the shielding room is grounded.

5. The ultrasonic therapy system as claimed in claim 1, wherein said electric control unit comprises an electric control unit for controlling the movement of a treatment bed; and wherein the electric control unit includes a position sensor which will de-energize the electric control unit after the treatment bed enters into an imaging area of the imaging device.

6. The ultrasonic therapy system of claim 5, wherein the electric control unit further comprises multiple low-pass filters, and the filters respectively filter the electromagnetic waves produced by a high-frequency generator which provides the power supply to the ultrasonic therapy applicator and the driving motors.

7. The ultrasonic therapy system of claim 6, wherein said filter has an attenuation rate ranging from 80 dB to 120 dB for the electromagnetic waves with a frequency higher than 10 MHz.

8. The ultrasonic therapy system of claim 6, wherein the outer shell of each driving motor is covered by a motor shielding cover which shields the electromagnetic waves; and a cutoff wave-guide pipe, which may bring attenuation to electromagnetic waves, is arranged on the output shaft of each driving motor, and the cutoff wave-guide pipe is connected to the motor shielding cover at one end and is grounded; with an anode and cathode of each driving motor respectively connected to a filter.

9. The ultrasonic therapy system of claim 8, wherein the driving motors and ultrasonic therapy applicator are placed in the shielding room of the imaging device, which shields the electromagnetic waves; firstly, the anode and cathode of each driving motor are respectively connected to a filter located in the shielding room and then said filter is connected to a filter located outside of the shielding room; the ultrasonic therapy applicator is connected to the high-frequency generator through a filter located outside of the shielding room; the motor shielding covers and the outer shells of the driving motors are respectively connected to the shielding room by way of single-point grounding, and the shielding room is grounded.

10. The ultrasonic therapy system of claim 8, wherein said cutoff wave-guide pipe has an attenuation rate ranging from 80 dB to 120 dB for the electromagnetic waves with a frequency lower than 100 MHz.

11. The ultrasonic therapy system as claimed in claim 1, wherein said imaging device adopts an MRI apparatus.

\* \* \* \* \*

UNITED STATES PATENT AND TRADEMARK OFFICE
CERTIFICATE OF CORRECTION

PATENT NO. : 8,463,356 B2
APPLICATION NO. : 12/445355
DATED : June 11, 2013
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1015 days.

Signed and Sealed this
Eighth Day of September, 2015

Michelle K. Lee
*Director of the United States Patent and Trademark Office*